(12) United States Patent
Sugahara (10) Patent No.: US 10,916,010 B2
(45) Date of Patent: Feb. 9, 2021

(54) LEARNING DATA CREATION SUPPORT APPARATUS, LEARNING DATA CREATION SUPPORT METHOD, AND LEARNING DATA CREATION SUPPORT PROGRAM

(71) Applicant: FUJIFILM Corporation, Tokyo (JP)

(72) Inventor: Masataka Sugahara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 79 days.

(21) Appl. No.: 16/274,723

(22) Filed: Feb. 13, 2019

(65) Prior Publication Data

US 2019/0266722 A1 Aug. 29, 2019

(30) Foreign Application Priority Data

Feb. 28, 2018 (JP) ................. 2018-035193

(51) Int. Cl.
| | |
|---|---|
| G06T 7/00 | (2017.01) |
| G06T 7/11 | (2017.01) |
| G16H 30/20 | (2018.01) |
| A61B 6/00 | (2006.01) |
| G16H 30/40 | (2018.01) |

(52) U.S. Cl.
CPC ............ *G06T 7/0012* (2013.01); *A61B 6/463* (2013.01); *A61B 6/5217* (2013.01); *G06T 7/11* (2017.01); *G16H 30/20* (2018.01); *G16H 30/40* (2018.01); *G06T 2207/20081* (2013.01); *G06T 2207/30096* (2013.01)

(58) Field of Classification Search
CPC ..................... G06T 7/0012; G06T 7/11; G06T 2207/20081; G06T 2207/30096; G06T 2207/10116; G06T 2207/10081; G06T 2207/10088; G06T 2207/10104; G06T 2207/10132; G06T 2207/30068; G06T 2207/20084; G16H 30/20; G16H 30/40; G16H 50/70; A61B 6/463; A61B 6/5217; A61B 6/502

See application file for complete search history.

(56) References Cited

U.S. PATENT DOCUMENTS

| | | | |
|---|---|---|---|
| 2005/0152592 A1 | 7/2005 | Kasai | |
| 2015/0261915 A1* | 9/2015 | Yanagida | G06F 19/321 382/131 |
| 2018/0150971 A1* | 5/2018 | Adachi | G06T 7/74 |
| 2020/0065970 A1* | 2/2020 | Sonoda | G06T 7/11 |
| 2020/0155870 A1* | 5/2020 | Takahashi | A61B 6/12 |

FOREIGN PATENT DOCUMENTS

JP     2005-185560 A    7/2005

* cited by examiner

*Primary Examiner* — Qian Yang
(74) *Attorney, Agent, or Firm* — Birch, Stewart, Kolasch & Birch, LLP (57) ABSTRACT

Provided is a technique that generates learning data required for learning without performing a complicated operation. Candidate positions of a plurality of lesion candidate region images obtained by performing an image analysis process for a medical image are displayed on schematic diagrams of a human body. Lesion candidate region images other than a lesion candidate region image corresponding to a denied candidate position where a denial operation has been received are registered as correct answer data or the lesion candidate region images corresponding to confirmed candidate positions where a confirmation operation has been received are registered as the correct answer data.

17 Claims, 6 Drawing Sheets

LEARNING DATA CREATION SUPPORT APPARATUS, LEARNING DATA CREATION SUPPORT METHOD, AND LEARNING DATA CREATION SUPPORT PROGRAM

CROSS REFERENCE TO RELATED APPLICATIONS

This application claims priority under 35 U.S.C § 119(a) to Patent Application No. 2018-035193 filed in Japan on Feb. 28, 2018, all of which are hereby expressly incorporated by reference into the present application.

BACKGROUND OF THE INVENTION

1. Field of the Invention

The present invention relates to a learning data creation support apparatus, a learning data creation support method, and a learning data creation support program that support the creation of learning data for a discriminator.

2. Description of the Related Art

In recent years, machine learning has been used in order to learn the characteristics of data and to recognize and classify, for example, images. In recent years, various learning methods have been developed and the processing time has been reduced with the improvement of the processing capability of computers. Therefore, it is possible to perform deep learning in which a system learns the characteristics of, for example, image data at a deeper level. The execution of deep learning makes it possible to recognize the characteristics of, for example, images with very high accuracy. The discrimination performance is expected to be improved.

In a medical field, artificial intelligence (AI) which performs learning using a deep learning method to recognize the characteristics of an image with high accuracy is preferable. In the deep learning, it is necessary to perform learning with a large amount of high-quality data suitable for the purpose. Therefore, it is important to efficiently prepare learning data. In each medical institution, image data for many cases is accumulated with the spread of a picture archiving and communication system (PACS). Therefore, a technique has been examined which performs learning using image data for various cases accumulated in each medical institution.

In addition, in the medical field, shadows, such as tumors appearing on an image, are classified into abnormal cases or normal cases in advance and the shadow images are learned as learning data to determine whether the shadows appearing on the image are normal or abnormal. For example, in JP2005-185560A, regions to be registered are designated on a displayed medical image and are classified into abnormal cases and normal cases and learning data is generated.

SUMMARY OF THE INVENTION

However, the operation of manually designating the region to be registered as the learning data on the medical image requires a lot of time and effort and it is difficult to generate a large amount of learning data.

In contrast, a radiologist interprets the image of a patient and makes an interpretation report. In a case in which the interpretation report is created, an image to be interpreted and a schema diagram are displayed and the radiologist operates a device, such as a mouse, to put a mark at a position where an abnormal shadow is present on the schema diagram while observing the image to be interpreted. Alternatively, a region including an abnormal shadow is automatically detected by an image analysis process and is displayed on the schema diagram. As such, the radiologist creates an interpretation report while performing an operation of specifying a lesion region appearing in a medical image or while determining whether a lesion candidate region extracted by the image analysis process is correct answer or incorrect answer.

The invention has been made in order to solve the above-mentioned problems and an object of the invention is to provide a learning data creation support apparatus, a learning data creation support method, and a learning data creation support program that automatically create learning data required for learning using an operation of making an interpretation report.

According to an aspect of the invention, there is provided a learning data creation support apparatus comprising: display means for displaying candidate positions of a plurality of lesion candidate region images obtained by performing an image analysis process for a medical image on a schematic diagram of a human body; and registration means for receiving an operation of denying a designated candidate position and registering, as correct answer data, lesion candidate region images other than a lesion candidate region image corresponding to a denied candidate position where the denial operation has been received, or receiving an operation of confirming a designated candidate position and registering, as the correct answer data, a lesion candidate region image corresponding to a confirmed candidate position where the confirmation operation has been received.

According to another aspect of the invention, there is provided a learning data creation support method performed in a learning data creation support apparatus. The learning data creation support method comprises: a display step of displaying candidate positions of a plurality of lesion candidate region images obtained by performing an image analysis process for a medical image on a schematic diagram of a human body; and a registration step of receiving an operation of denying a designated candidate position and registering, as correct answer data, lesion candidate region images other than a lesion candidate region image corresponding to a denied candidate position where the denial operation has been received, or receiving an operation of confirming a designated candidate position and registering, as the correct answer data, a lesion candidate region image corresponding to a confirmed candidate position where the confirmation operation has been received.

According to still another aspect of the invention, there is provided a learning data creation support program that causes a computer to perform: a display step of displaying candidate positions of a plurality of lesion candidate region images obtained by performing an image analysis process for a medical image on a schematic diagram of a human body; and a registration step of receiving an operation of denying a designated candidate position and registering, as correct answer data, lesion candidate region images other than a lesion candidate region image corresponding to a denied candidate position where the denial operation has been received, or receiving an operation of confirming a designated candidate position and registering, as the correct answer data, a lesion candidate region image corresponding to a confirmed candidate position where the confirmation operation has been received.

The "lesion candidate region" means a region that is likely to be a lesion on the medical image and indicates a region that is likely to be a lesion extracted by the image analysis process of the computer. In addition, the "lesion candidate region image" means an image portion including the lesion candidate region in the entire medical image.

The "schematic diagram of the human body" means a diagram that distinctively indicates the characteristics of the outer shape, organs, or tissues of the human body.

The "correct answer data" means data in which a correct answer label is attached to the lesion candidate region image. In a case in which the lesion candidate region image is determined to be an image including a lesion, the lesion candidate region image is correct answer data.

The registration means may register, as incorrect answer data, the lesion candidate region image corresponding to the denied candidate position in a case in which the denial operation has been received and lesion candidate region images other than the lesion candidate region image corresponding to the confirmed candidate position in a case in which the confirmation operation has been received.

The "incorrect answer data" means data in which an incorrect answer label is attached to the lesion candidate region image. In a case in which the lesion candidate region image is determined not to be an image including a lesion, the lesion candidate region image is incorrect answer data.

Preferably, marks are provided at a plurality of candidate positions on the schematic diagram of the human body and the denial operation is an operation of removing the mark displayed at the candidate position.

Marks may be provided at a plurality of candidate positions on the schematic diagram of the human body and the learning data creation support apparatus may further comprise report recording means for including a schematic diagram in which the marks are put at the candidate positions other than the denied candidate position in a case in which the denial operation has been received in an interpretation report and recording the interpretation report, or including a schematic diagram in which the mark is put at the confirmed candidate position in a case in which the confirmation operation has been received in an interpretation report and recording the interpretation report.

Preferably, in a case in which the image analysis process is a process of detecting the lesion candidate region image with a discriminator that has learned the correct answer data, the learning data creation support apparatus further comprises learning means for causing the discriminator to relearn the registered correct answer data.

Preferably, in a case in which the image analysis process is a process of detecting the lesion candidate region image with at least one of a discriminator that has learned the correct answer data or a discriminator that has learned the incorrect answer data, the learning data creation support apparatus further comprises learning means for causing the discriminator to relearn at least one of the registered correct answer data or the registered incorrect answer data.

The schematic diagram may be a schema diagram.

According to yet another aspect of the invention, there is provided a learning data creation support apparatus comprising: a memory that stores commands for causing a computer to perform processes; and a processor that is configured to execute the stored commands. The processor displays candidate positions of a plurality of lesion candidate region images obtained by performing an image analysis process for a medical image on a schematic diagram of a human body. In addition, the processor receives an operation of denying a designated candidate position and registers, as correct answer data, lesion candidate region images other than a lesion candidate region image corresponding to a denied candidate position where the denial operation has been received, or receives an operation of confirming a designated candidate position and registers, as the correct answer data, a lesion candidate region image corresponding to a confirmed candidate position where the confirmation operation has been received.

According to the invention, the candidate positions of a plurality of lesion candidate region images obtained by performing an image analysis process for a medical image are displayed on a schematic diagram of a human body. An operation of denying a designated candidate position is received and lesion candidate region images other than a lesion candidate region image corresponding to a denied candidate position are registered as correct answer data. Alternatively, an operation of confirming a designated candidate position is received and a lesion candidate region image corresponding to a confirmed candidate position is registered as the correct answer data. Therefore, the operator can create learning data required for learning, without performing a special operation for creating the learning data, for the operation of determining whether a candidate position on a schematic diagram is correct in a case in which an interpretation report is made.

DESCRIPTION OF THE PREFERRED EMBODIMENTS

Figure 1:
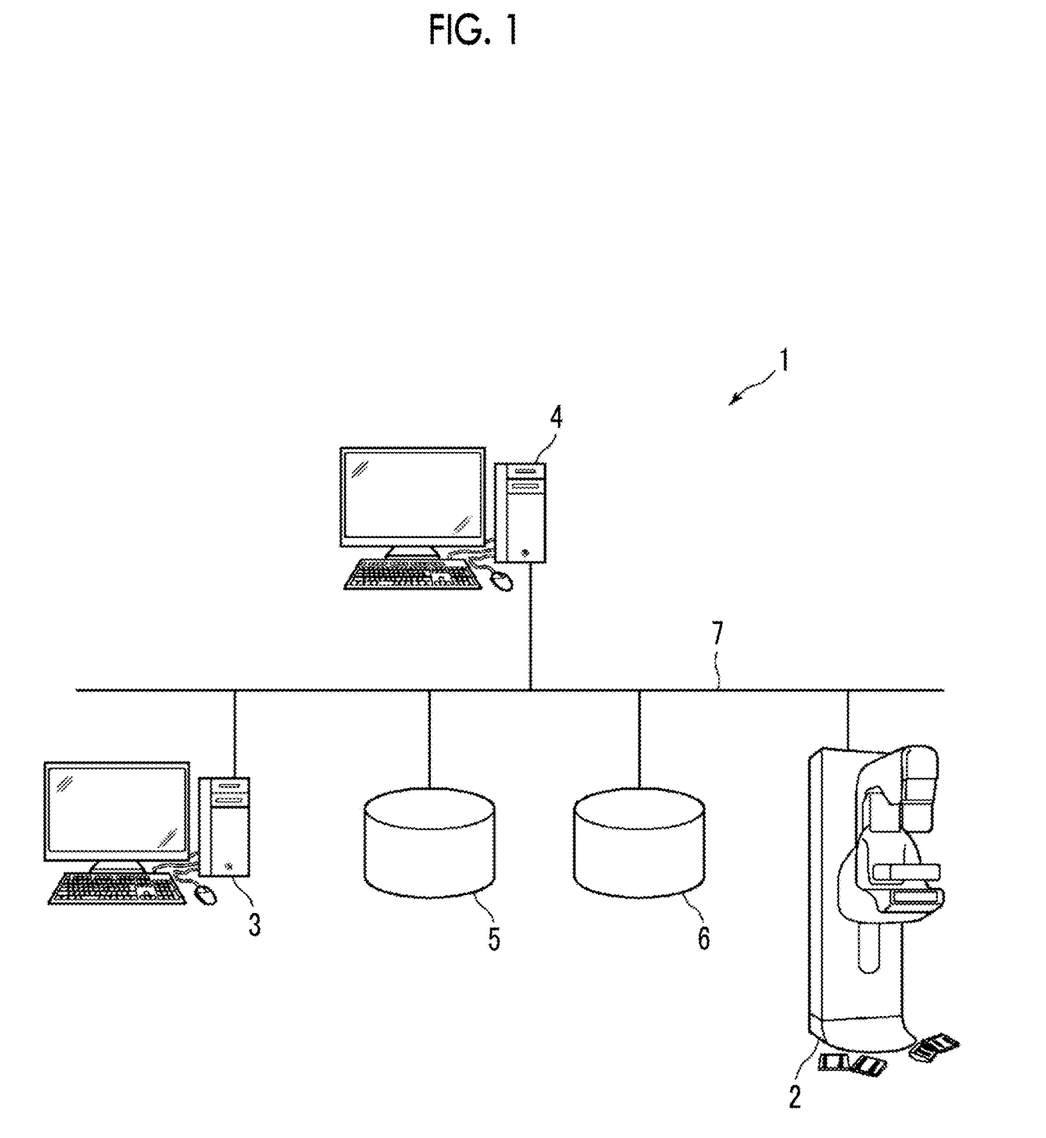
FIG. 1 is a diagram schematically illustrating the configuration of a medical information system.

Hereinafter, a first embodiment of the invention will be described with reference to the drawings. FIG. 1 illustrates the schematic configuration of a medical information system 1 provided with a learning data creation support apparatus according to the first embodiment of the invention.

The medical information system 1 is used to capture an image of an examination target part of a subject and to store the image on the basis of an examination order from a doctor in the diagnosis and treatment department and is used by a radiologist in the radiology department to interpret the captured image and to make an interpretation report. As illustrated in FIG. 1, the medical information system 1 is configured by connecting a modality 2, a radiologist workstation 3, a diagnosis and treatment department workstation 4, an image database 5, and an interpretation report database 6 so as to communicate with each other through a network 7. An application program that causes each apparatus to function as a component of the medical information system 1 is installed in each apparatus. In addition, the application program may be installed from a recording medium, such as a digital versatile disc (DVD) or a compact disc read only memory (CD-ROM), or may be downloaded from a storage device of a server connected through a network, such as the Internet, and then installed.

The modality 2 includes an apparatus that captures an image of an examination target part of the subject, generates an examination image indicating the part, adds accessory information defined by a digital imaging and communication in medicine (DICOM) standard to the image, and outputs the image. Examples of the modality include a mammography apparatus, a computed tomography (CT) apparatus, a magnetic resonance imaging (MM) apparatus, a positron emission tomography (PET) apparatus, an ultrasound apparatus, and a computed radiography (CR) apparatus using a flat panel detector (FPD).

Figure 2:
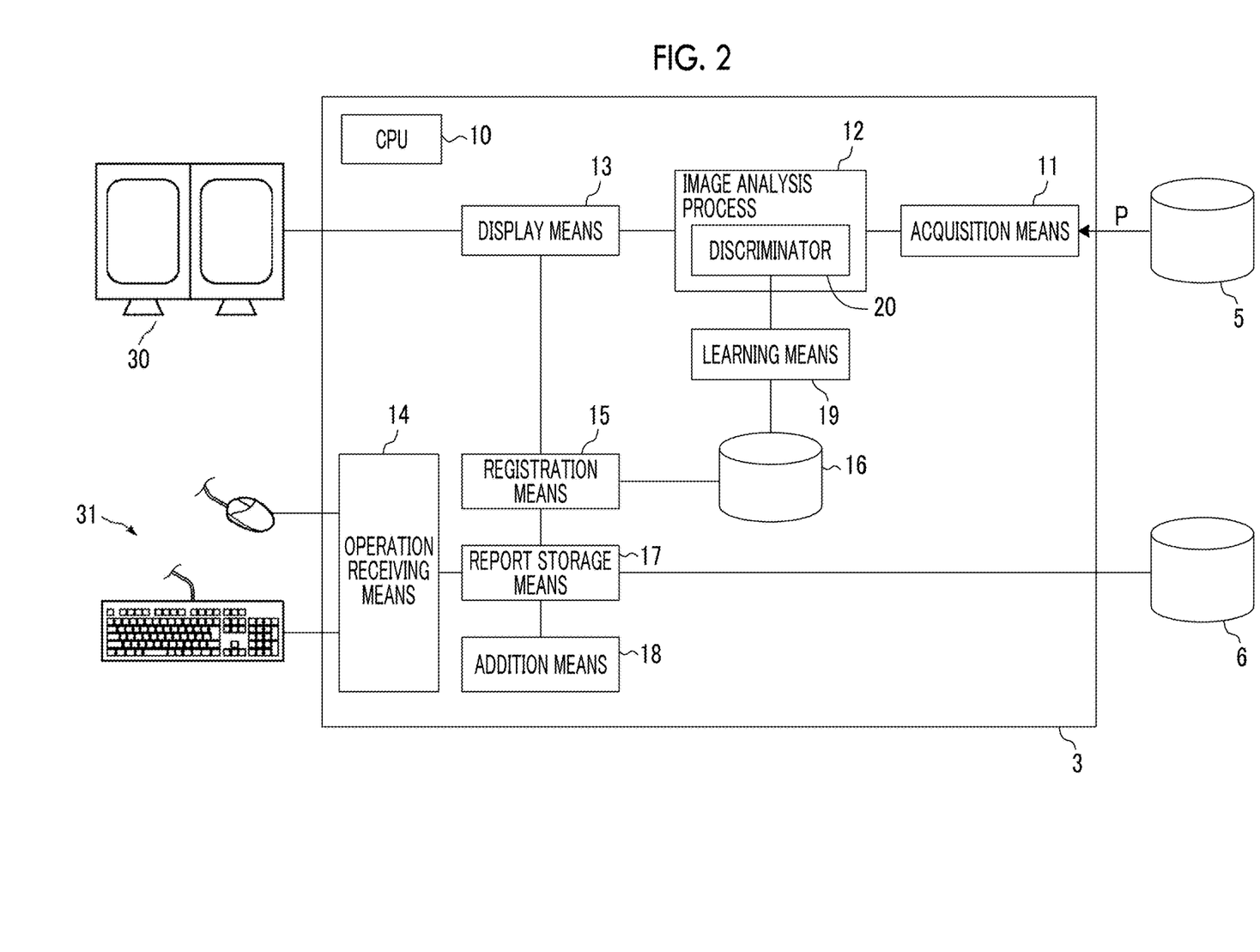
FIG. 2 is a diagram schematically illustrating the configuration of a learning data creation support apparatus according to the invention.

The radiologist workstation 3 (hereinafter, the radiologist workstation is referred to as a radiologist WS 3) is a computer that is used by a radiologist in the radiology department to interpret an image and to make an interpretation report and comprises known hardware configurations, such as a central processing unit (CPU) 10, a main storage device, an auxiliary storage device, an input/output interface, a communication interface, a display device 30, an input device 31, and a data bus as illustrated in FIG. 2. For example, a known operation system is installed in the radiologist WS 3. The radiologist WS 3 includes one high-definition display or a plurality of high-definition displays as the display device 30. In the radiologist WS 3, processes, such as the display of an image received from the image database 5, image processing including the automatic detection and highlight display of a portion that appears to be a lesion in the image, and the making and display of an interpretation report, are performed by executing software programs for each process. In addition, in the radiologist WS 3, the input device 31 including, for example, a keyboard and a mouse, is used to input an interpretation report on an interpretation target. In a case in which the input of the interpretation report is completed, the radiologist WS 3 requests the registration of the interpretation report to the interpretation report database 6 through the network 7.

For example, the diagnosis and treatment department workstation 4 (hereinafter, the diagnosis and treatment department workstation is referred to as a diagnosis and treatment department WS 4) is a computer that is used by a doctor in the diagnosis and treatment department to observe an image in detail, to read an interpretation report, to read an electronic chart, and to input an electronic chart and comprises known hardware configurations, such as a CPU, a main storage device, an auxiliary storage device, an input/output interface, a communication interface, an input device, a display device, and a data bus. For example, a known operation system is installed in the diagnosis and treatment department WS 4 and the diagnosis and treatment department WS 4 includes one high-definition display or a plurality of high-definition displays as the display device. In the diagnosis and treatment department WS 4, processes, such as the display of an image received from the image database 5, the automatic detection or highlight display of a portion that appears to be a lesion in the image, and the display of an interpretation report received from the interpretation report database 6, are performed by executing software programs for each process.

A software program that provides the functions of a database management system (DBMS) to a general-purpose computer is incorporated into the image database 5 and the image database 5 comprises a high-capacity storage. The storage may be a high-capacity hard disk drive, a network attached storage (NAS) connected to the network 7, or a disk device connected to a storage area network (SAN). In addition, image data captured by the modality 2 is transmitted to the image database 5 through the network 7 according to a storage format and a communication standard based on the DICOM standard and is then stored in the image database 5. The examination images of a plurality of patients captured by the modality 2 and accessory information are registered in the image database 5. For example, an image identification (ID) for identifying an individual image, a patient ID for identifying a subject, the imaging date and time when the examination image was generated, the type of modality used in the examination for acquiring the examination image, patient information including the name, age, and sex of the patient, and an examination part (imaging part) are recorded on the accessory information.

A software program that provides the functions of a database management system (DBMS) to a general-purpose computer is incorporated into the interpretation report database 6 and the interpretation report database 6 comprises a high-capacity storage. The storage may be a high-capacity hard disk drive, a NAS connected to the network 7, or a disk device connected to a SAN. For example, an interpretation report on which information including an image ID for identifying an interpretation target image, a radiologist ID for identifying the radiologist who has interpreted images, a lesion name, a lesion region, the positional information of a lesion, and the doctor's opinion has been recorded is registered in the interpretation report database 6.

The network 7 is a local area network that connects various apparatuses in the hospital. In a case in which the radiologist WS 3 is installed in another hospital or a medical office, the network 7 may be configured by connecting the local area networks of each hospital with the Internet or a leased line. In any case, preferably, the network 7 is, for example, an optical network that can transmit the examination image at a high speed.

In addition, a learning data creation support program is installed in the radiologist WS 3 such that the radiologist WS 3 functions as a learning data creation support apparatus according to the embodiment of the invention. The learning data creation support program may be stored in a storage device of a computer connected to the network or may be stored in a network storage such that it can be accessed from the outside, may be downloaded to the radiologist WS 3, and may be installed in the radiologist WS 3. Alternatively, the learning data creation support program may be recorded on a recording medium, such as a DVD or a CD-ROM, may be distributed, and may be installed in a computer from the recording medium.

In a case in which the radiologist WS 3 is executed, the learning data creation support program is stored in the main storage device (not illustrated) and the CPU 10 performs these processes according to the program stored in the main storage device such that the radiologist WS 3 functions as the learning data creation support apparatus. Hereinafter, the radiologist WS 3 will be described as the learning data creation support apparatus 3.

First, the functions of the learning data creation support apparatus 3 will be described. As illustrated in FIG. 2, the learning data creation support apparatus 3 functions as acquisition means 11, image analysis means (hereinafter, referred to as an image analysis process) 12, display means 13, operation receiving means 14, registration means 15, a learning data storage unit 16, report recording means 17, addition means 18, and learning means 19.

The acquisition means 11 acquires a medical image P to be interpreted among the images captured according to an examination order issued from the doctor in the diagnosis and treatment department from the image database 5.

The image analysis process 12 is provided with a discriminator 20, discriminates a shadow that appears in the medical image P acquired by the acquisition means 11 using the discriminator 20, detects lesion candidate regions, such as a tumor and calcification, and acquires information related to the positions of the lesion candidate regions as candidate positions. The candidate position may be acquired as a coordinate value in the medical image P. The candidate position may be information in which an anatomical position is known or information indicating an upper part, a middle part, or a lower part of each organ. For example, in the case of the breast, the candidate position is information indicating an inner upper part, an inner lower part, an outer upper part, an outer lower part, an areola part of each of the right and left breasts. In the case of the abdomen, for example, the candidate position is information indicating an upper right abdominal part, an upper left abdominal part, the pit of the stomach, the navel, a right abdominal part, a left abdominal part, a lower right abdominal part, and a lower left abdominal part.

The display means 13 puts marks indicating the candidate positions of a plurality of lesion candidate regions obtained by performing the image analysis process on the medical image P to be interpreted to a schematic diagram of a human body and displays a plurality of candidate positions on the display device 30. The schematic diagram of the human body is, for example, a diagram illustrating the shape of the entire human body, a diagram illustrating the characteristics of a part of the human body (for example, the abdomen, the chest, or the head), a diagram illustrating the outline or characteristics of organs (for example, the stomach, the intestines, the liver, the kidney, the lungs, and the breast), or a diagram illustrating the shape of tissues (for example, bones, blood vessels, and lymph). In addition, the schematic diagram of the human body is a diagram that illustrates a body part and can be used by a doctor to make a medical record or an interpretation report. Specifically, the schematic diagram is, for example, a schema diagram. Hereinafter, a case in which a schema diagram is used as the schematic diagram will be described.

In addition, positions on the schema diagram and the anatomical positions (for example, a coordinate value in the medical image P or the upper part, the middle part, or the lower part of each organ) of the human body are associated with each other in advance. The display means 13 puts marks at each candidate position according to the plurality of lesion candidate regions obtained by the image analysis process 12 and the anatomical positions (hereinafter, referred to as candidate positions) of the lesion candidate regions and displays the candidate positions on the schema diagram. In addition, it is preferable to change the type of mark, for example, the shape, size, or color of the mark depending on the type of lesion that appears in an image portion (hereinafter, referred to as a lesion candidate region image) of the medical image P including the detected lesion candidate region.

Figure 3:
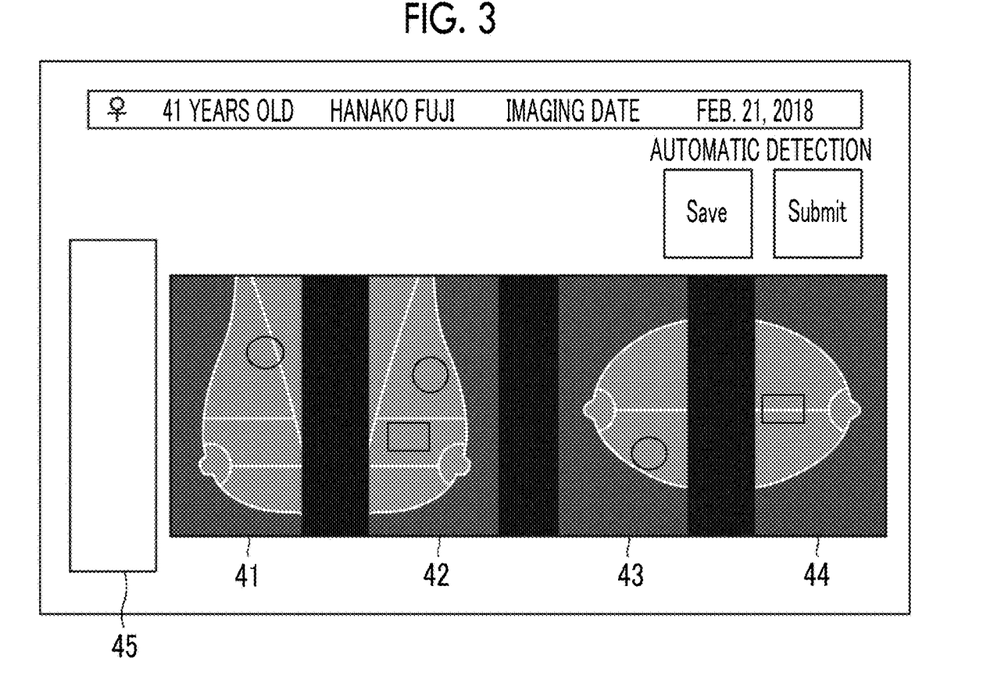
FIG. 3 illustrates an example of the display of marks on a schema diagram.
Figure 4:
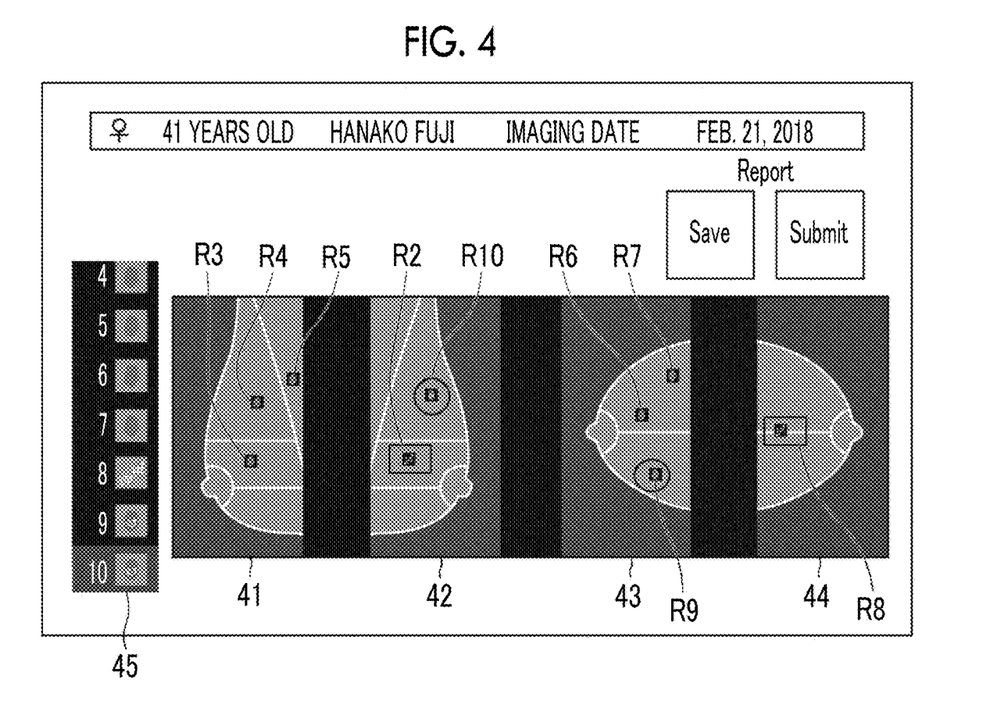
FIG. 4 is a diagram illustrating an operation in a case in which an interpretation report is made using the schema diagram.

FIGS. 3 and 4 illustrate an example of a breast schema diagram. In the case of the breast, the breast schema diagram includes four schema diagrams, that is, schema diagrams 41 and 42 illustrating the outward shape of the breast in a case in which the images of each of the left and right breasts are captured by mediolateral oblique (MLO) mammography and schema diagrams 43 and 44 illustrating the outward shape of the breast in a case in which the images of each of the left and right breasts are captured by craniocaudal (CC) mammography. Marks are displayed at the candidate positions detected by the image analysis process 12 on the schema diagrams 41, 42, 43, and 44. FIG. 3 illustrates an example in which circular and rectangular marks are put at the candidate positions on the schema diagrams 41, 42, 43, and 44 of the breast. The circular mark indicates the candidate position of a tumor and the rectangular mark indicates the candidate position of calcification. In addition, as illustrated in FIG. 4, minified images R2 to R10 of the lesion candidate region images of the medical image P may be used as the marks indicating the candidate positions.

The operation receiving means 14 receives an input corresponding to the operation of the user, such as a radiologist, through the input device 31 and determines the type of the received operation. Examples of the operation include an operation of denying the candidate position where a lesion candidate is present, an operation of confirming the candidate position where a lesion candidate is present, and an operation of adding a candidate position. The operation of denying the candidate position is performed in a case in which the user determines that the lesion candidate region of the medical image P corresponding to the position of the mark on the schema diagram is not a lesion. The mark corresponding to the candidate position is removed and the image corresponding to the candidate position is registered as incorrect answer data. In contrast, the operation of confirming the candidate position is performed in a case in which the user determines that the lesion candidate region of the medical image P corresponding to the position of the mark on the schema diagram is a lesion. The image corresponding to the candidate position is registered as correct answer data. In addition, the operation of adding a candidate position is performed in a case in which a mark is not put at a position on the schema diagram corresponding to a position where a lesion appears in the medical image P.

Specifically, for example, the operation receiving means 14 determines an operation of designating and removing the mark on the schema diagram to be the operation of denying the candidate position. In contrast, in a case in which only the operation of selecting a mark is performed, the operation receiving means 14 determines the operation to be the operation of confirming the candidate position. Alternatively, the candidate position where the operation of removing the mark on the schema diagram has not been performed is confirmed, the operation of confirming the candidate position may not be defined. In addition, an operation of specifying a position without a mark on the schema diagram (for example, an operation of clicking the position of a lesion on the schema diagram) may be determined to be the operation of adding the candidate position.

Alternatively, in a case in which an operation of designating a mark on the schema diagram and clicking the right mouse button is performed, the operation may be determined to be the operation of confirming the candidate position. In a case in which an operation of clicking the left mouse button is performed, the operation may be determined to be the operation of denying the candidate position. Hereinafter, the candidate position where the denial operation has been performed is referred to as a denied candidate position and the candidate position where the confirmation operation has been performed is referred to as a confirmed candidate position. In addition, in a case in which the operation for the schema diagram is completed while the candidate position where neither the confirmation operation nor the denial operation has been clearly performed remains, it is preferable that the candidate position is determined to be the confirmed position.

The addition means 18 adds a candidate position and a lesion candidate region image corresponding to the candidate position according to the candidate position addition operation received by the operation receiving means 14. For example, the addition means 18 adds the anatomical position information of the position where the candidate position addition operation has been performed as the candidate position and adds a mark to the candidate position on the schema diagram. In addition, the addition means 18 adds, as the lesion candidate region image, an image portion on which the user has performed an operation of using, for example, the mouse to draw a circle surrounding a shadow that appears to be a lesion on the medical image P with a cursor.

FIG. 4 illustrates an example of a screen in a case in which the user makes a report while observing the medical image P. A list of thumbnail images which are the minified images of the lesion candidate region images is displayed in a frame 45 that is disposed on the right side of the screen. A circular mark is displayed in the schema diagram 41 of the left breast (MLO) illustrated in FIG. 3. However, in a case in which a lesion is not recognized at that position of the medical image P, the circular mark is removed as illustrated in FIG. 4. In the schema diagram 42 of the right breast (MLO), the schema diagram 43 of the left breast (CC), and the schema diagram 44 of the right breast (CC) illustrated in FIG. 4, the minified images of the lesion candidate region images corresponding to the candidate positions R2, R8, R9, and R10 of the circular and rectangular marks are displayed at the candidate positions. In addition, the candidate positions are added to the schema diagrams 41, 43, and 44 and the minified images of the lesion candidate region images are displayed at the added candidate positions R3, R4, R5, R6, and R7.

In addition, the operation receiving means 14 receives the input of, for example, an operation related to the input of the doctor's opinion, such as the characteristics of a shadow and a diagnosis name, and an operation of recording a report. In the example illustrated in FIG. 4, in a case in which the user selects a "SAVE" button disposed on the upper right side, the report that has been made is recorded.

The registration means 15 registers the correct answer data and the incorrect answer data according to the operation received by the operation receiving means 14. Specifically, the registration means 15 registers, as the correct answer data, lesion candidate region images other than the lesion candidate region image corresponding to the denied candidate position where the operation of denying the designated candidate position has been received or registers, as the correct answer data, the lesion candidate region image corresponding to the confirmed candidate position where the operation of confirming the designated candidate position has been received. In addition, the registration means 15 registers, as the incorrect answer data, the lesion candidate region image corresponding to the denied candidate position or lesion candidate region images other than the lesion candidate region image corresponding to the confirmed candidate position.

For example, in a case in which the user performs only the operation of removing the candidate position, that is, the operation of denying the candidate position and ends the input operation without performing the operation of confirming the candidate position, the registration means 15 registers, as the correct answer data, the lesion candidate region image corresponding to the candidate position from which the mark has not been removed on the schema diagram and registers, as the incorrect answer data, the lesion candidate region image corresponding to the candidate position from which the mark has been removed on the schema diagram.

Alternatively, as in the case in which, if the user designates a mark on the schema diagram and performs the operation of clicking the right mouse button, the operation is determined to be the operation of confirming the candidate position and, if the user clicks the left mouse button, the operation is determined to be the operation of denying the candidate position, in a case in which both the confirmation operation and the denial operation are performed, the registration means 15 may register, as the correct answer data, the lesion candidate region image corresponding to the candidate position where the confirmation operation has been received and may register, as the incorrect answer data, the lesion candidate region image corresponding to the candidate position where the denial operation has been received.

In addition, the registration means 15 registers the lesion candidate region image added by the addition means 18 as the correct answer data.

In a case in which the incorrect answer data is not used for the learning operation of the discriminator, the registration means 15 may not register the lesion candidate region image corresponding to the incorrect answer data.

The learning data storage unit 16 is provided in an auxiliary storage device such as a hard disk or an SSD. Alternatively, the learning data storage unit 16 may be provided in a NAS connected to the network.

In addition, a correct answer data label or an incorrect answer data label is attached to the lesion candidate region image and the lesion candidate region image is stored as learning data in the learning data storage unit 16. Further, a correct answer data label is attached to the added lesion region image and the added lesion region image is stored as the learning data.

In a case in which the operation receiving means 14 receives an operation of recording a report, the report recording means 17 includes the schema diagram in which marks have been put at the candidate positions other than the denied candidate position in an interpretation report and records the interpretation report. Alternatively, the report recording means 17 includes the schema diagram in which a mark has been put at the confirmed candidate position in an interpretation report and records the interpretation report. That is, the report recording means 17 includes the schema diagram, in which a mark at the confirmed candidate position among the marks on the schema diagram and the added mark have been put, in the interpretation report and records the interpretation report. For example, marks other than the mark on which the mark removal operation has been performed on the schema diagram remain and the report recording means 17 includes the schema diagram, in which the added mark has been put, in a report and records the report. The recorded interpretation report is transmitted to the interpretation report database 6 and is then stored therein.

The learning means 19 directs the discriminator 20 to relearn the correct answer data and the incorrect answer data stored in the learning data storage unit 16. The image analysis process 12 detects a lesion candidate region using the discriminator that has learned the correct answer data and the incorrect answer data in advance. Since the correct answer data and the incorrect answer data obtained by, for example, the radiologist who has determined whether the detected lesion candidate region is a lesion are relearned, it is possible to improve the discrimination performance. In a case in which a certain amount of learning data has been accumulated, it is preferable that the discriminator 20 learns the correct answer data and the incorrect answer data to update the image analysis process 12. In addition, in a case in which learning is performed, the learning may be performed using only the correct answer data or only the incorrect answer data.

Figure 5:
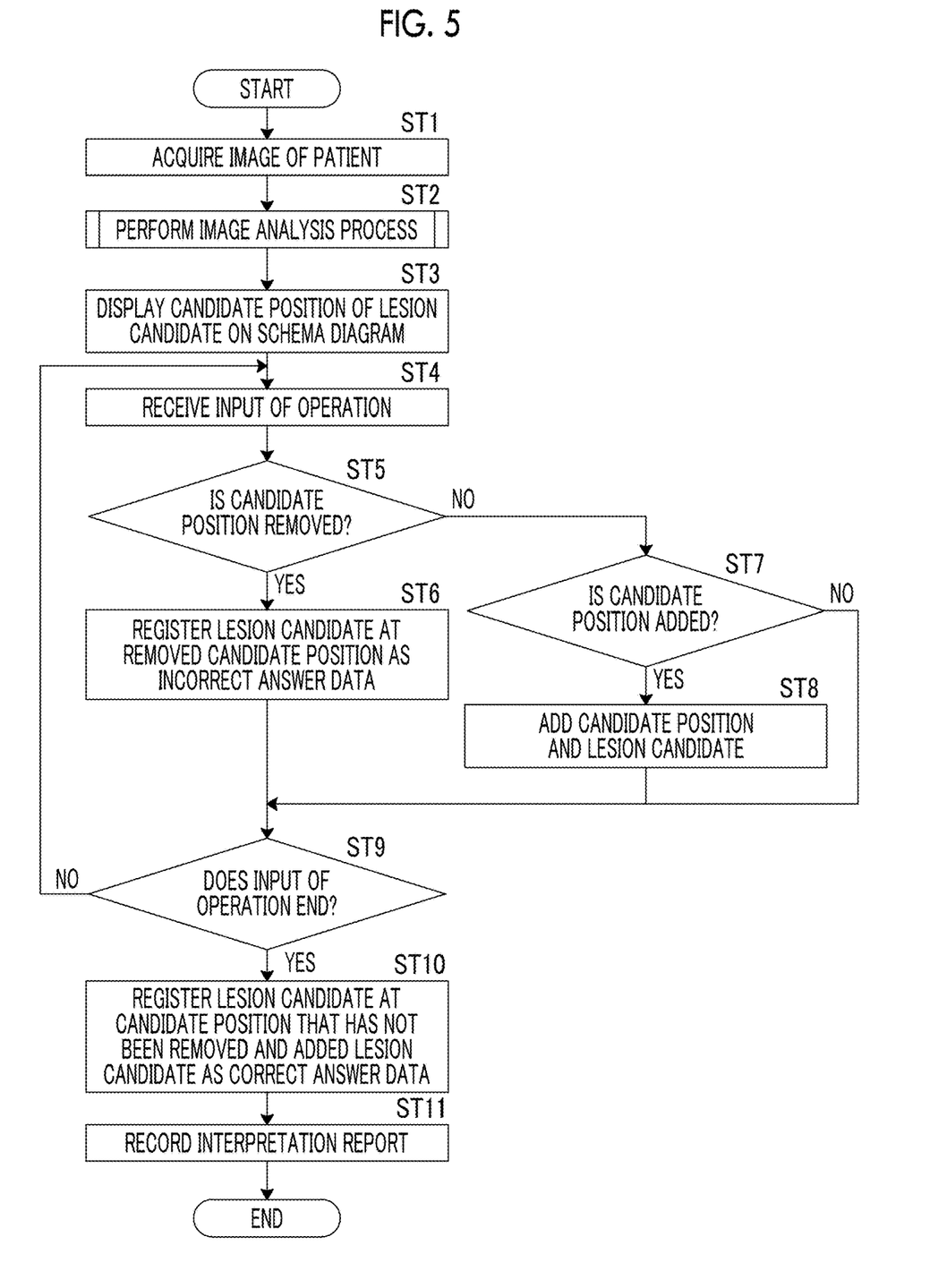
FIG. 5 is a flowchart illustrating the flow of a learning data registration process according to a first embodiment.

FIG. 5 is a flowchart illustrating the flow of the process of the radiologist WS 3. A method for creating learning data using the operation of the user in a case in which the user observes a breast image and makes an interpretation report will be described according to the flowchart illustrated in FIG. 5. In addition, in this embodiment, a case in which two displays are provided as the display device 30 will be described.

First, in a case in which the user inputs a patient ID of an interpretation target using the input device 31, such as a keyboard, the acquisition means 11 acquires the medical image P corresponding to the patient ID from the image database 5 (Step ST1). Then, a screen for making a report which corresponds to a part included in the medical image P is displayed on one display and the medical image P is displayed on the other display. For example, in a case in which the part included in the medical image P is the breast, the schema diagram illustrated in FIG. 3 is displayed on the screen for making a report. In addition, the image analysis process 12 is performed for the acquired medical image P to detect lesion candidate regions from the medical image P (Step ST2). As illustrated in FIG. 3, the display means 13 displays circular and rectangular marks at the candidate positions of the lesion candidate regions detected by the image analysis process 12 on the schema diagrams 41, 42, 43, and 44 (Step ST3).

The user performs, for example, an operation of removing or adding the candidate position on the schema diagrams 41, 42, 43, and 44 with the input device 31, such as a mouse, while observing the medical image P displayed on the display. For example, in a case in which the user determines that a lesion is not recognized at a position corresponding to the candidate position indicated by a circular mark on the upper part of the left breast in the schema diagram 41 illustrated in FIG. 3 in the medical image P, the user performs an operation of selecting the circular mark and removing the candidate position. The operation receiving means 14 receives the input of an operation (Step ST4). In a case in which the input operation is an operation of removing the candidate position, the determination result in Step ST5 is "YES". In addition, as illustrated in FIG. 4, the circular mark in the left breast of the schema diagram 41 illustrated in FIG. 3 is removed. Then, the registration means 15 registers the lesion candidate region image corresponding to the removed candidate position as the incorrect answer data in the learning data storage unit 16 (Step ST6). Then, until it is determined that the input of an operation ends in Step ST9, the process returns to Step ST4 and the input of the next operation is received.

In a case in which the user observes the medical image P and finds a shadow that appears to be a lesion at a position without any mark other than the position with the circular mark in the schema diagram 41 illustrated in FIG. 3, the user performs an operation of specifying a position on the schema diagram corresponding to the shadow with, for example, the mouse. For example, the user moves the cursor to a position on the right side of the nipple of the left breast on the schema diagram 41 illustrated in FIG. 3 and clicks the mouse. Since the input operation received by the operation receiving means 14 does not correspond to the operation of removing the candidate position, the determination result in Step ST5 is "NO". Then, it is determined whether the input operation is the operation of adding a candidate position (Step ST7). Since a position without a candidate position mark on the schema diagram 41 is clicked, the operation is determined to be the operation of adding a candidate position and the determination result in Step ST7 is "YES". In addition, as illustrated in FIG. 4, the candidate position R3 corresponding to the position indicated by the addition means 18 is added to the schema diagram 41. Then, in a case in which the user performs an operation of drawing a circle surrounding a shadow of a lesion, which is located at a position corresponding to the candidate position R3, on the medical image P with, for example, the mouse, the addition means 18 adds the surrounded image portion as the lesion candidate region image (Step ST8). In addition, as illustrated in FIG. 4, a minified image of the lesion candidate region is displayed at the candidate position R3 of the schema diagram 41. Until it is determined that the input of an operation ends in Step ST9, the process returns to Step ST4 and the input of the next operation is received.

In a case in which interpretation is completed, the user presses a "SAVE" button illustrated in FIG. 4 to record the interpretation report. The input operation received by the operation receiving means 14 is determined to be the end of the input of the operation corresponding to the interpretation report (the determination results in Step ST5 and Step ST7 are "NO") and the determination result in Step ST9 is "YES". Then, the lesion candidate region image corresponding to the candidate position which has not been removed by the registration means 15 and the lesion candidate region image corresponding to the added candidate position are registered as the correct answer data in the learning data storage unit 16 (Step ST10).

In addition, the report recording means 17 includes the schema diagram with the mark corresponding to the candidate position which has not been removed and the mark (minified image) corresponding to the added candidate position in the interpretation report and records the interpretation report (Step ST11).

As described in detail above, the user can perform a removal operation to register an unnecessary lesion candidate image as the incorrect answer data and can register a necessary lesion candidate region image as the correct answer data, without performing both the operation of confirming a mark corresponding to a necessary candidate position and the operation of removing an unnecessary position, during the operation of making an interpretation report while observing the medical image P. In addition, for the region from which the lesion candidate region image has not been extracted by image analysis, the lesion candidate region image can be added to the correct answer data by the addition operation.

Figure 6:
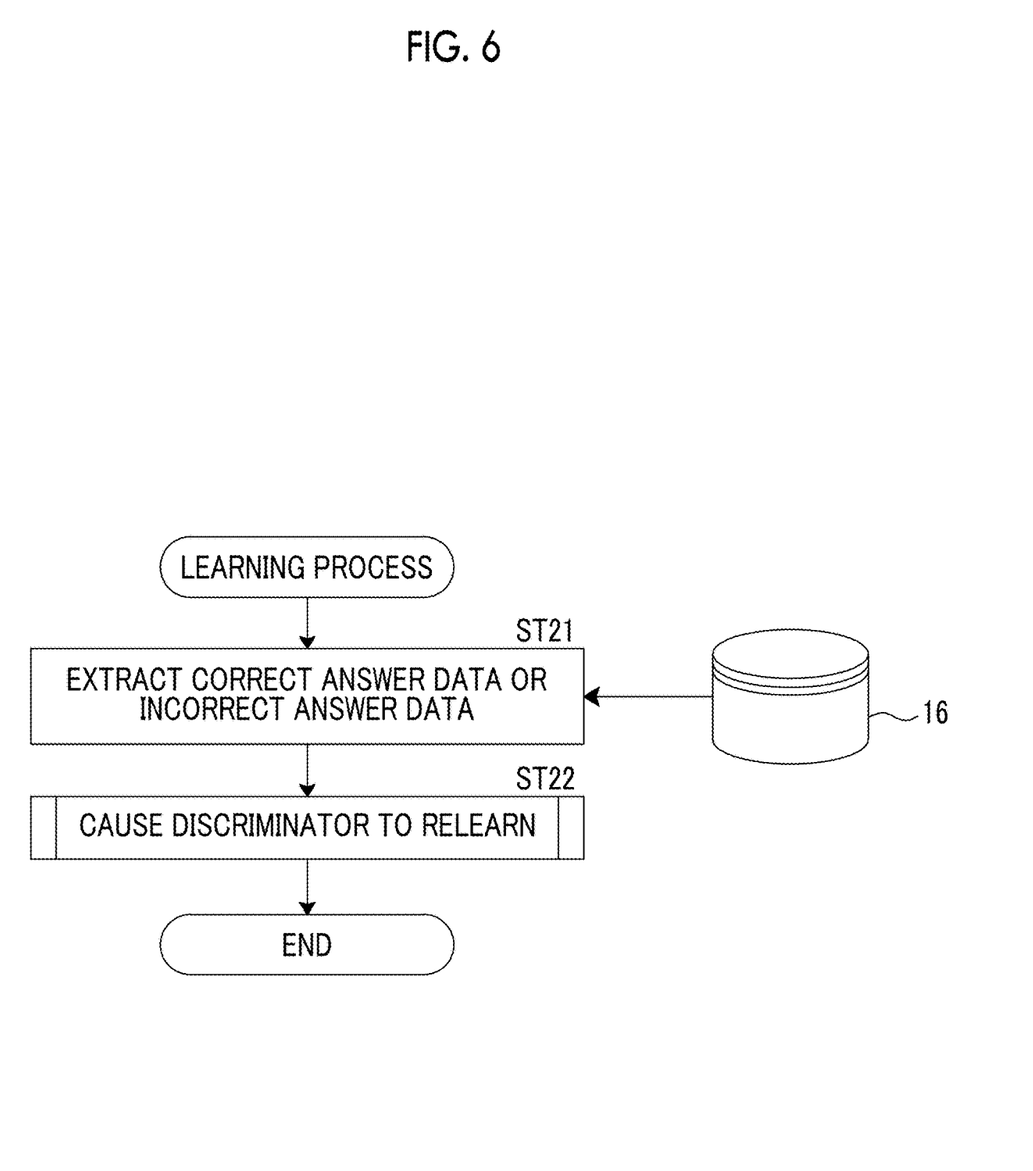
FIG. 6 is a flowchart illustrating the flow of a process of learning a discriminator.

Next, the flow of a process for causing the discriminator 20 of the image analysis process 12 to perform learning using the correct answer data and the incorrect answer data accumulated in the learning data storage unit 16 will be described with reference to the flowchart of a learning process illustrated in FIG. 6.

In a case in which a certain amount of learning data is accumulated, the correct answer data and the incorrect answer data are extracted from the learning data storage unit 16 (Step ST21) and the discriminator performs relearning (Step ST22). The discriminator that has performed the relearning is incorporated into the image analysis process 12 and the image analysis process 12 is reinstalled in the radiologist WS 3.

As such, since the correct answer data and the incorrect answer data determined by the radiologist are learned, it is possible to improve the discrimination performance of the image analysis process.

Next, a second embodiment of the invention will be described with reference to the drawings. Since a medical information system 1 according to the second embodiment of the invention is the same as that according to the first embodiment illustrated in FIG. 1, the detailed description thereof will not be repeated. In addition, since the schematic configuration of a learning data creation support apparatus 3 according to the second embodiment is the same as that of the learning data creation support apparatus 3 according to the first embodiment illustrated in FIG. 2, the detailed description thereof will not be repeated.

In the first embodiment, the case in which only the operation of removing the mark on the schema diagram, that is, only the operation of denying the candidate position is performed has been described. However, in the second embodiment, a case in which both the operation of confirming the candidate position and the operation of denying the candidate position are performed will be described according to a flowchart illustrated in FIG. 7.

In a case in which an operation of designating a mark on the schema diagram and clicking the right mouse button is performed, the operation receiving means 14 according to this embodiment determines that the operation is an operation of confirming the candidate position. In a case in which an operation of designating a mark on the schema diagram and clicking the left mouse button is performed, the operation receiving means 14 determines that the operation is an operation of denying the candidate position.

Figure 7:
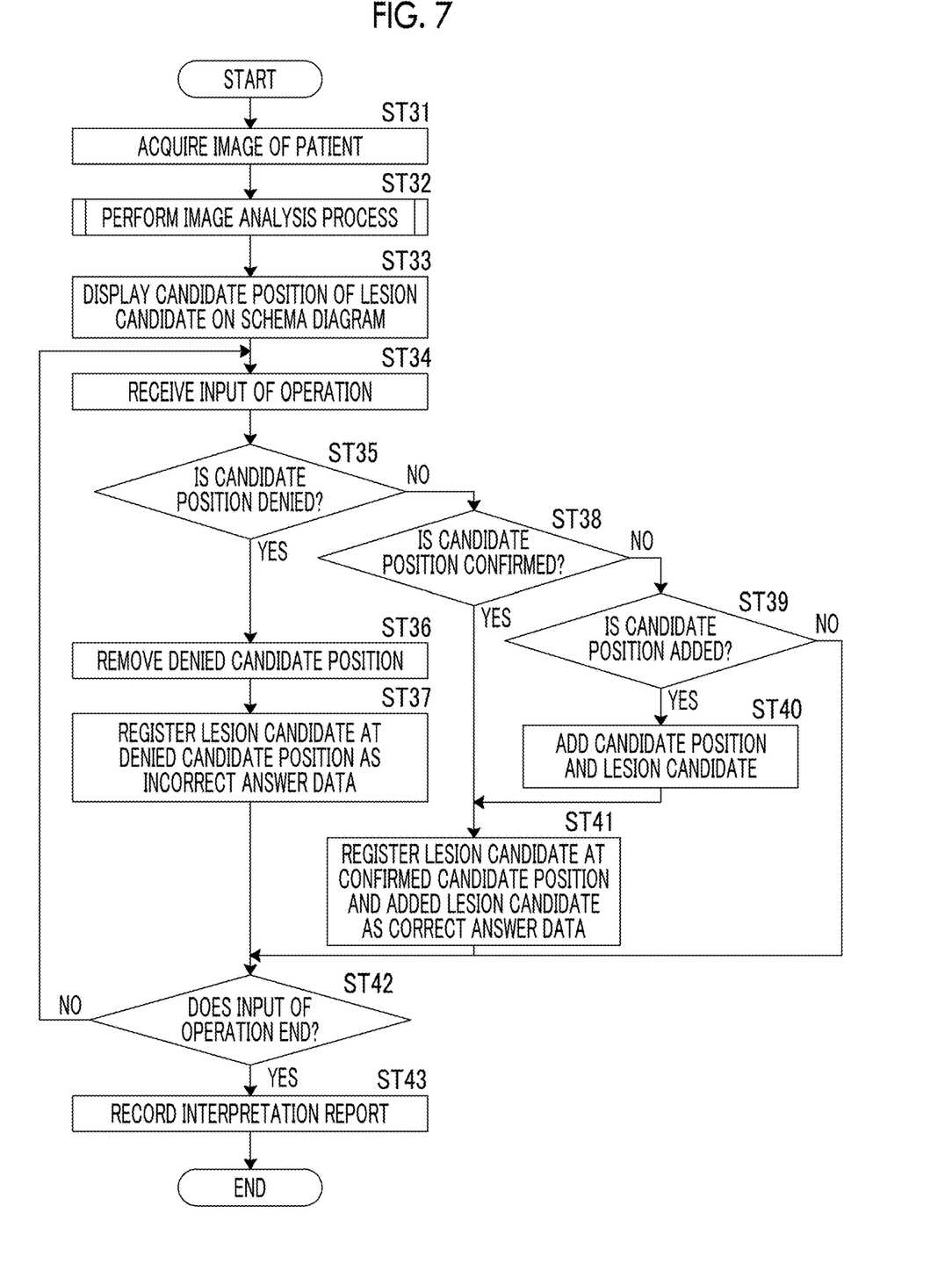
FIG. 7 is a flowchart illustrating the flow of a learning data registration process according to a second embodiment.

FIG. 7 is a flowchart illustrating the flow of the process of the radiologist WS 3 according to the second embodiment. Since a process in Steps ST31 to ST33 is the same as the process in Steps ST1 to ST3 according to the first embodiment, the detailed description thereof will not be repeated.

In a case in which Steps ST31 to ST33 are performed, the schema diagrams 41, 42, 43, and 44 are displayed on the screen of one display and the medical image P is displayed on the screen of the other display. The operation receiving means 14 receives the input of the operation of the user for the schema diagrams 41, 42, 43, and 44 through the input device 31 such as a mouse (Step ST34). In a case in which the user selects, for example, the circular mark in the upper part of the left breast in the schema diagram 41 of FIG. 3 and clicks the left mouse button, the operation is determined to be the operation of denying the candidate position and the determination result in Step ST35 is "YES". In addition, as illustrated in FIG. 4, the circular mark in the schema diagram 41 illustrated in FIG. 3 is removed (Step ST36). Then, the registration means 15 registers the lesion candidate region image corresponding to the candidate position indicated by the removed mark as the incorrect answer data (Step ST37). Until interpretation ends and it is determined that the input of the operation ends in Step ST42, the process returns to Step ST34 and the input of the next operation is received.

Then, in a case in which the user selects the circular mark in the upper part of the right breast in the schema diagram 42 and clicks the right mouse button, the operation is determined to be the operation of confirming the candidate position (the determination result in Step ST35 is "NO" and the determination result in Step ST38 is "YES"). In addition, as illustrated in FIG. 4, the minified image of the lesion candidate region image corresponding to the candidate position indicated by the right-clicked circular mark on the schema diagram 42 is displayed in the circle. In addition, the registration means 15 registers the lesion candidate region image corresponding to the confirmed candidate position as the correct answer data (Step ST41). Until it is determined that the input of the operation ends in Step ST42, the process returns to Step ST34 and the input of the next operation is received.

Alternatively, in a case in which the user observes the medical image P and finds a shadow that appears to be a lesion at a position other than the position with the circular mark in the schema diagram 41 illustrated in FIG. 3, the user performs an operation of specifying a position on the right side of the nipple on the schema diagram 41 which corresponds to the shadow with, for example, the mouse. In a case in which the input operation received by the operation receiving means 14 is determined to be the operation of adding the candidate position (the determination results in Steps ST35 and ST38 are "NO" and the determination result in Step ST39 is "YES", the mark of the candidate position R3 corresponding to the position indicated by the addition means 18 is added to the schema diagram 41 (Step ST40). Then, in a case in which the user performs an operation of drawing a circle surrounding a shadow that appears to be a lesion on the medical image P with, for example, the mouse, the addition means 18 adds the surrounded image portion as the lesion candidate region image (Step ST40). The registration means 15 registers the added lesion candidate region image as the correct answer data (Step ST41). Until it is determined that the input of an operation ends in Step ST42, the process returns to Step ST34 and the input of the next operation is received.

In a case in which interpretation ends, the user presses the "SAVE" button to record the interpretation report. The input operation received by the operation receiving means 14 is determined to be the end of the input of the operation corresponding to the interpretation report (the determination results in Step ST35, Step ST38, and Step ST39 are "NO") and the determination result in Step ST42 is "YES".

Then, the report recording means 17 includes the schema diagrams 41, 42, 43, and 44 in which marks have been put at the right-clicked candidate position and the added candidate position in the interpretation report and records the interpretation report (Step ST43).

As described in detail above, the user can perform both the operation of confirming the candidate position detected by the image analysis process and the operation of denying the candidate position during the operation of making an interpretation report while observing the medical image P. Therefore, it is possible to reliably attach a correct answer data label and an incorrect answer data label to the lesion candidate region image without waiting for the end of the input of all of the operations.

Since a process for causing the discriminator of the image analysis process according to the second embodiment to learn is the same as that in the first embodiment, the detailed description thereof will not be repeated.

As described in the first and second embodiments, learning data is created while an interpretation report is being made and the discriminator of the image analysis process learns the learning data. Therefore, it is possible to improve the discrimination performance at any time.

In the first and second embodiments, the case in which a candidate position without a mark among the candidate positions on the schema diagram is specified and added has been described. However, an image portion in which the user has performed an operation of drawing a circle surrounding a shadow that appears to be a lesion in a region without a candidate position on the medical image P may be added to the lesion candidate region image and a candidate position mark may be automatically displayed at a position corresponding to the position on the schema diagram.

In the first and second embodiments, the case in which the image analysis process is provided in the radiologist WS 3 has been described. However, the image analysis process may be provided in an image processing server connected through the network. In this case, the schema diagram is displayed on the basis of the result of the image analysis process obtained through the network. In addition, the discriminator may perform relearning in the image processing server.

In each of the above-described embodiments, the hardware structure of a processing unit that performs various processes of the learning data creation support apparatus is the following various processors. The various processors include a central processing unit (CPU) which is a general-purpose processor that executes software (program) to function as various processing units, a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process.

One processing unit may be formed by one of the various processors or may be formed by a combination of two or more processors of the same type or different types (for example, a combination of a plurality of FPGAs or a combination of a CPU and an FPGA). In addition, a plurality of processing units may be formed by one processor. A first example of the configuration in which the plurality of processing units are formed by one processor is an aspect in which one or more CPUs and software are combined to form one processor and the processor functions as a plurality of processing units. A representative example of the aspect is a computer such as a client apparatus or a server. A second example of the configuration is an aspect in which a processor that implements all of the functions of a system including the plurality of processing units with one integrated circuit (IC) chip is used. A representative example of the aspect is a system-on-chip (SoC). As such, the hardware structure of various processing units is formed by using one or more of the various processors.

EXPLANATION OF REFERENCES

1: medical information system
2: modality
3: learning data creation support apparatus
3: radiologist workstation
4: diagnosis and treatment department workstation
5: image database
6: interpretation report database
7: network
11: acquisition means
12: image analysis process
13: display means
14: operation receiving means
15: registration means
16: learning data storage unit
17: report recording means
18: addition means
19: learning means
20: discriminator
30: display device
31: input device
41, 42, 43, 44: schema diagram
45: minified image display frame

What is claimed is:

1. A learning data creation support apparatus comprising:
   a display displays candidate positions of a plurality of lesion candidate region images obtained by performing an image analysis process for a medical image on a schematic diagram of a human body; and
   a processor configured to,
      receive a designation of a denial operation to all of at least one of the candidate positions that are denied; and
      after receiving a designation of the denial operation, register, as correct answer data, lesion candidate region images other than a lesion candidate region image corresponding to the at least one denied candidate positions where the denial operation has been received,
   wherein the processor further registers, as incorrect answer data, the lesion candidate region image corresponding to the at least one denied candidate positions and lesion candidate region images other than the lesion candidate region image corresponding to a confirmed candidate position.

2. The learning data creation support apparatus according to claim 1,
   wherein marks are provided at a plurality of candidate positions on the schematic diagram of the human body, and
   the denial operation is an operation of removing the mark displayed at the candidate position.

3. The learning data creation support apparatus according to claim 2,
   wherein marks are provided at a plurality of candidate positions on the schematic diagram of the human body, and
   the processor further configured to
      record a schematic diagram in which the marks are put at candidate positions other than the at least one denied candidate positions in a case in which the denial operation has been received in an interpretation report, or
      record a schematic diagram in which the mark is put at the confirmed candidate position in a case in which the confirmation operation has been received in an interpretation report.

4. The learning data creation support apparatus according to claim 2,
   wherein the schematic diagram is a schema diagram.

5. The learning data creation support apparatus according to claim 1,
   wherein marks are provided at a plurality of candidate positions on the schematic diagram of the human body, and
   the denial operation is an operation of removing the mark displayed at the candidate position.

6. The learning data creation support apparatus according to claim 1,
   wherein marks are provided at a plurality of candidate positions on the schematic diagram of the human body, and
   the processor further configured to
      record a schematic diagram in which the marks are put at candidate positions other than the at least one denied candidate positions in a case in which the denial operation has been received in an interpretation report, or record a schematic diagram in which the mark is put at the confirmed candidate position in a case in which the confirmation operation has been received in an interpretation report.

7. The learning data creation support apparatus according to claim 6,
wherein the schematic diagram is a schema diagram.

8. The learning data creation support apparatus according to claim 1,
wherein marks are provided at a plurality of candidate positions on the schematic diagram of the human body, and
the processor further configured to
record a schematic diagram in which the marks are put at candidate positions other than the at least one denied candidate positions in a case in which the denial operation has been received in an interpretation report, or
record a schematic diagram in which the mark is put at the confirmed candidate position in a case in which the confirmation operation has been received in an interpretation report.

9. The learning data creation support apparatus according to claim 1,
wherein the image analysis process is a process of detecting the lesion candidate region image with a discriminator that has learned the correct answer data, and
the processor further configured to cause the discriminator to relearn the registered correct answer data.

10. The learning data creation support apparatus according to claim 9,
wherein the schematic diagram is a schema diagram.

11. The learning data creation support apparatus according to claim 1,
wherein the image analysis process is a process of detecting the lesion candidate region image with at least one of a discriminator that has learned the correct answer data or a discriminator that has learned the incorrect answer data, and
the processor further configured to cause the discriminator to relearn at least one of the registered correct answer data or the registered incorrect answer data.

12. The learning data creation support apparatus according to claim 11,
wherein the schematic diagram is a schema diagram.

13. The learning data creation support apparatus according to claim 1,
wherein the schematic diagram is a schema diagram.

14. The learning data creation support apparatus according to claim 1,
wherein the schematic diagram is a schema diagram.

15. A learning data creation support method performed in a learning data creation support apparatus, the method comprising:
displaying candidate positions of a plurality of lesion candidate region images obtained by performing an image analysis process for a medical image on a schematic diagram of a human body;
receiving a designation of a denial operation to all of at least one of the candidate positions that are denied and after receiving a designation of the denial operation, registering, as correct answer data, lesion candidate region images other than a lesion candidate region image corresponding to the at least one denied candidate positions where the denial operation has been received, and
registering, as incorrect answer data, the lesion candidate region image corresponding to the at least one denied candidate positions and lesion candidate region images other than the lesion candidate region image corresponding to a confirmed candidate position.

16. A non-transitory computer readable recording medium storing a learning data creation support program that causes a computer to:
display candidate positions of a plurality of lesion candidate region images obtained by performing an image analysis process for a medical image on a schematic diagram of a human body;
receive a designation of a denial operation to all of at least one of the candidate positions that are denied and after receiving a designation of the denial operation, registering, as correct answer data, lesion candidate region images other than a lesion candidate region image corresponding to the at least one denied candidate positions where the denial operation has been received, and
register, as incorrect answer data, the lesion candidate region image corresponding to the at least one denied candidate positions and lesion candidate region images other than the lesion candidate region image corresponding to a confirmed candidate position.

17. A learning data creation support apparatus comprising:
a memory that stores commands for causing a computer to perform processes; and
a processor that is configured to execute the stored commands,
wherein the processor displays candidate positions of a plurality of lesion candidate region images obtained by performing an image analysis process for a medical image on a schematic diagram of a human body, and
the processor receives a designation of a denial operation to all of at least one of the candidate positions that are denied; and after receiving a designation of the denial operation, registers, as correct answer data, lesion candidate region images other than a lesion candidate region image corresponding to the at least one denied candidate positions where the denial operation has been received,
wherein the processor further registers, as incorrect answer data, the lesion candidate region image corresponding to the at least one denied candidate positions and lesion candidate region images other than the lesion candidate region image corresponding to a confirmed candidate position.

* * * * *